United States Patent
Tsujita et al.

(10) Patent No.: US 6,610,682 B2
(45) Date of Patent: Aug. 26, 2003

(54) PHARMACEUTICAL COMPOSITIONS AND METHODS FOR THE TREATMENT OF ARTERIOSCLEROSIS

(75) Inventors: Yoshio Tsujita, Ichikawa (JP); Toshihiko Fujiwara, Ebina (JP); Toshio Sada, Tokyo (JP); Naoyuki Maeda, Zushi (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/933,922

(22) Filed: Aug. 21, 2001

(65) Prior Publication Data

US 2002/0013308 A1 Jan. 31, 2002

Related U.S. Application Data

(63) Continuation of application No. 09/231,052, filed on Jan. 14, 1999, which is a continuation-in-part of application No. PCT/JP97/02407, filed on Jul. 11, 1997.

(30) Foreign Application Priority Data

Jul. 15, 1996 (JP) .............................. 8-184368

(51) Int. Cl.⁷ ..................... A61K 31/554; A61K 31/47; A61K 31/401; A61K 31/198
(52) U.S. Cl. .................. 514/211.07; 514/221; 514/307; 514/423; 514/396; 514/561; 514/824; 514/91; 514/108; 514/543
(58) Field of Search .......................... 514/824, 91, 108, 514/423, 543, 211.07, 221, 307, 396, 561

(56) References Cited

U.S. PATENT DOCUMENTS

| | | | |
|---|---|---|---|
| 5,223,522 A | | 6/1993 | Clark et al. |
| 5,231,080 A | | 7/1993 | Scholkens |
| H1286 H | * | 2/1994 | Eisman et al. ................. 514/91 |
| 5,298,497 A | | 3/1994 | Tschollar et al. |
| 5,461,039 A | | 10/1995 | Tschollar et al. |
| 5,593,971 A | | 1/1997 | Tschollar et al. |
| 5,616,599 A | | 4/1997 | Yanagisawa et al. |
| 5,646,171 A | | 7/1997 | Yanagisawa et al. |
| 5,668,117 A | | 9/1997 | Shapiro |
| 6,107,323 A | | 8/2000 | Tamura et al. |

FOREIGN PATENT DOCUMENTS

| | | |
|---|---|---|
| EP | 219 782 | 4/1987 |
| EP | 332 332 | 9/1989 |
| EP | 411 395 | 2/1991 |
| EP | 425 956 | 5/1991 |
| EP | 426066 | 5/1991 |
| EP | 503785 | 9/1992 |
| EP | 603 419 | 6/1994 |
| EP | 861666 | 9/1998 |
| GB | 2241890 | 9/1991 |
| JP | 7-41423 | 2/1995 |
| WO | WO 94/19347 | 9/1994 |
| WO | WO 95/26188 | 10/1995 |
| WO | WO97/37688 | 10/1997 |

OTHER PUBLICATIONS

Allan J. Naftilan, "Angiotensin II Induces c–fos Expression in Smooth Muscle Via Transcriptional Control", *Hypertension*, 13, 706–711 (1989).

H.W. Farber et al., "Components of the Angiotensin System Cause Release of a Neutrophil Chemoattractant from Cultured Bovine and Human Endothial Cells", *Eur. Heart J.*, 11, (Suppl. B), 100–107 (1990).

Gunnar Aberg and Patricia Ferrer, "Effects of Captopril on Atherosclerosis in Cynomolgus Monkeys", *J. Cardiovasc. Pharmacol.* 15, S65–S72 (1990).

Yasuo Akanuma et al., Clinical Evaluation of a New Oral Hypoglycemic Agent CS–045 in Patients with Non–Insulin Dependent Diabetes Mellitus Poorly Controlled by Sulfonylureas–A Dose–Finding Study by Dose Increasing Method, *J. Clinical Therapeutic & Medicines*, 9, (Suppl. 3), 39–60 (1993).

Toru Murakami and Nobuhiro Yamada, "Can ACE Inhibitors Prevent Arteriosclerosis?", *Strides of Medicine*, 174, 810–813 (1995).

Gerald M. Reaven, "Role of Insulin Resistance in Human Disease", *Diabetes*, 37, 1595–1607 (1988).

Yoshio Watanabe et al., "Preventive Effect of Pravastatin Sodium, a Potent Inhibitor of 3–Hydroxy–3–Methylglutaryl Coenzymes A Reductase, on Coronary Atherosclerosis and Xanthoma in WHHL Rabbits", *Biochim. Biophys. Acta.*, 960, 294–203 (1988).

Aram V. Chobanian et al., "Antiatherogenic Effect of Captropril in the Watanabe Heritable Hyperlipidemic Rabbit", *Hypertension*, 15, 327–331 (1990).

*Jpn. Circ. J.*, 60, (Suppl. 1), 332 (No. 1137) (1996).

* cited by examiner

Primary Examiner—Samuel Barts
Assistant Examiner—Devesh Khare
(74) Attorney, Agent, or Firm—Frishauf, Holtz, Goodman & Chick, P.C.

(57) ABSTRACT

A pharmaceutical composition comprising as its active ingredients one or more drugs selected from the group consisting of angiotensin II receptor antagonists and angiotensin converting enzyme inhibitors, and one or more insulin resistance improving agents exhibits excellent arteriosclerotic progress inhibitory effects, and is useful as a drug, particularly as a drug for the prevention or treatment of arteriosclerosis. The invention also provides a method for the treatment or prophylaxis of arteriosclerosis by administering in combination (i) at least one of said angiotensin II receptor antagonists or angiotensin converting enzyme inhibitors and (ii) one or more insulin resistance improving agents to a mammal suffering from or susceptible to arteriosclerosis. The invention also provides kits containing at least a first container which comprises at least one angiotensin II receptor antagonists and/or angiotensin converting enzyme inhibitor and a second container which contains at least one insulin resistance improving agent.

86 Claims, No Drawings

PHARMACEUTICAL COMPOSITIONS AND METHODS FOR THE TREATMENT OF ARTERIOSCLEROSIS

This application is a continuation application of application Ser. No. 09/231,052 filed Jan. 14, 1999 which is a continuation-in-part application of International Application PCT/JP97/02407 filed Jul. 11, 1997 (not published in English).

The present invention relates to a pharmaceutical composition comprising as its active ingredients one or more drugs selected from the group consisting of angiotensin II receptor antagonists and angiotensin converting enzyme inhibitors, and one or more insulin resistance improving agents (particularly a pharmaceutical composition for prevention or treatment of arteriosclerosis), a kit including a first container comprising one or more drugs selected from the group consisting of angiotensin II receptor antagonists and angiotensin converting enzyme inhibitors, and a second container comprising one or more insulin resistance improving agents for preparing a pharmaceutical composition (particularly a composition for prevention or treatment of arteriosclerosis), and a method which comprises administering in combination effective amounts of one or more drugs selected from the group consisting of angiotensin II receptor antagonists and angiotensin converting enzyme inhibitors, and one or more insulin resistance improving agents to warm-blooded animals for preventing or treating diseases (particularly arteriosclerosis).

BACKGROUND OF THE INVENTION

The occurrence of atherosclerosis is increasing with the adoption of Western-style diet and the growth of the aged population. This disease is the main cause of such disorders as myocardial infarction, cerebral infarction and cerebral apoplexy, and there is a need for its effective prevention and treatment. Examples of risk factors which cause atherosclerosis include hyperlipemia (particularly hypercholesterolemia), hypertension and saccharometabolism disorders based on insulin resistance. In addition, there are many cases in which these risk factors occur in the form of complications (Syndrome X), and are considered to be mutually interrelated Diabetes, 37, 1595–1607 (1988).

Efforts have been made for the purpose of preventing and treating atherosclerosis by suppression of various risk factors such as hyperlipemia, hypertension and insulin resistance. Although HMG-CoA reductase inhibitors like pravastatin improve hyperlipemia, their inhibitory activity on arteriosclerosis in a case of administration alone is not enough, Biochim. Biophys. Acta, 960, 294–302 (1988). In addition, even insulin resistance improving agents like troglitazone do not exhibit sufficient atherosclerosis inhibitory activity in a case of administration alone (Japanese Patent Application (Kokai) No. Hei 7-41423).

On the other hand, among drugs for the treatment of hypertension, it has been reported that atherosclerotic lesions are suppressed when angiotensin converting enzyme (ACE) inhibitors that inhibit the renin-angiotensin system Hypertension, 15, 327–331 (1990) or angiotensin II receptor antagonists Jpn. Circ. J., 60 (Suppl. I), 332 (1996) are administered to animals having normal blood pressure and hypercholesterolemia. Angiotensin II not only exhibits vasoconstrictive activity, but also activity that stimulates the production of growth factors such as PDGF Hypertension, 13, 706–711 (1989) and activity that stimulates migration of neutrophils and macrophages Eur. Heart J., 11, 100–107 (1990). Although the mechanism in which renin-angiotensin system inhibitors suppress atherosclerosis is not clear at the present time, there is a possibility that the mechanism for suppressing atherosclerosis may be a function at the site of the lesion which is different from their blood pressure lowering action. However, since inhibitors of renin-angiotensin system are unable to lower serum lipids J. Cardiovasc. Pharmacol., 15, S65–S72 (1990), their administration alone has limitations on the treatment of arteriosclerosis.

In addition, although troglitazone, glibenclamide and captopril are administered concomitantly to diabetes patients, there is no suggestion indicated whatsoever relating to the prevention and treatment of arteriosclerosis J. Clinical Therapeutic & Medicines, 9 (Supp. 3), 39–60 (1933).

SUMMARY OF THE INVENTION

As a result of earnestly conducting various research in consideration of the importance of the prevention and treatment of arteriosclerosis, the inventors of the present invention found a method to solve the above-mentioned problems involved in the prior art and to obtain a preventive and/or therapeutic effect on arteriosclerosis by using the combination of one or more drugs selected from the group consisting of angiotensin II receptor antagonists and angiotensin converting enzyme inhibitors, and of one or more of insulin resistance improving agents.

The present invention provides a pharmaceutical composition comprising as its active ingredients one or more drugs selected from the group consisting of angiotensin II receptor antagonists and angiotensin converting enzyme inhibitors, and one or more insulin resistance improving agents (particularly a pharmaceutical composition for prevention or treatment of arteriosclerosis); a kit including a first container comprising one or more drugs selected from the group consisting of angiotensin II receptor antagonists and angiotensin converting enzyme inhibitors, and a second container comprising one or more insulin resistance improving agents for prevention or treatment of arteriosclerosis; a method which comprises administering in combination effective amounts of one or more drugs selected from the group consisting of angiotensin II receptor antagonists and angiotensin converting enzyme inhibitors, and one or more insulin resistance improving agents to warm-blooded animals for prevention or treatment of diseases (particularly arteriosclerosis); or a pharmaceutical composition for administering at the same time or at a different time one or more drugs selected from the group consisting of angiotensin II receptor antagonists and angiotensin converting enzyme inhibitors, and one or more insulin resistance improving agents (particularly a pharmaceutical composition for prevention of treatment of arteriosclerosis).

The active ingredients of the pharmaceutical composition of the present invention (particularly a pharmaceutical composition for the prevention or treatment of arteriosclerosis), or the active ingredients of a method for preventing or treating diseases (particularly arteriosclerosis) include one or more drugs selected from the group consisting of angiotensin II receptor antagonists and angiotensin converting enzyme inhibitors, and one or more insulin resistance improving agents.

Representative examples of angiotensin II receptor antagonists as an active ingredient of the present invention include biphenyltetrazole compounds and biphenylcarboxylic acid compounds described in Japanese Patent Application (Kokai) No. Hei 5-78328, Japanese Patent Application (Kokai) No. Sho 63-23868, Japanese Patent Application (Kokai) No. Hei 4-364171, Japanese Patent Application (Kokai) No. Hei 4-159718 or Japanese PCT Application (Kokai) No. Hei 4-506222, preferably biphenyltetrazole compounds, more preferably CS-866, losartan, candesartan, valsartan or irbesartan, still more preferably CS-866, losartan or candesartan, and most preferably CS-866.

The following indicates the chemical planar structural formulae of some typical examples of angiotensin II receptor antagonists.

CS-866

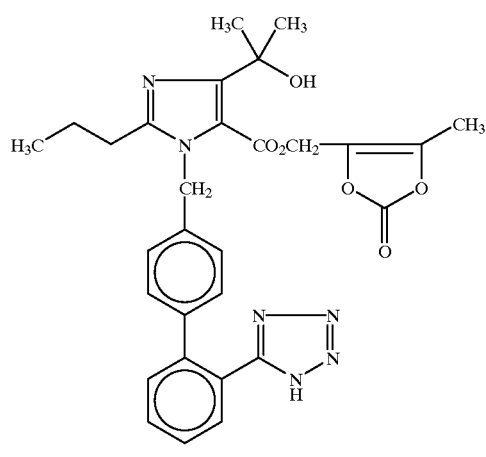

Losartan

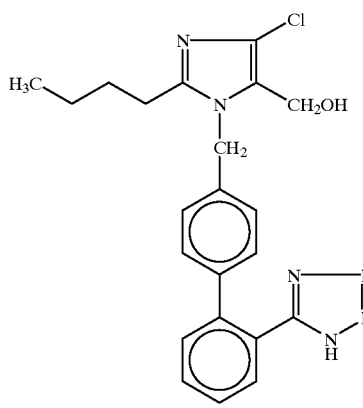

Candesartan

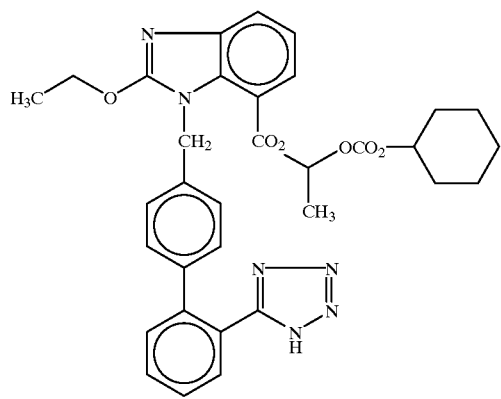

Valsartan

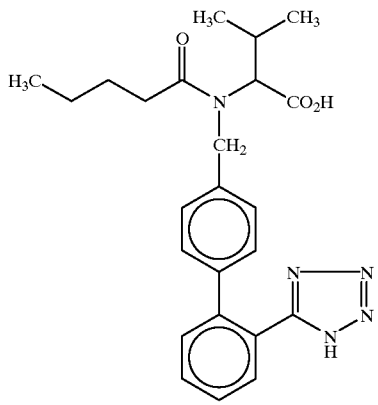

Irbesartan

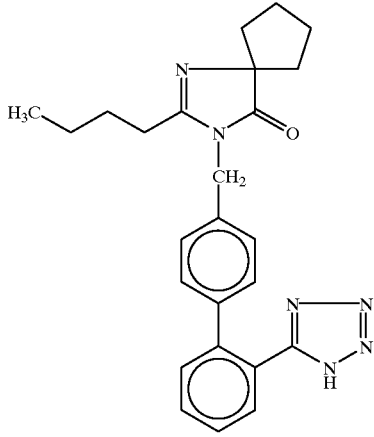

CS-866 is described in Japanese Patent Application No. (Kokai) No. Hei 5-78328 and the like, and its chemical name is (5-methyl-2-oxo-1,3-dioxolen-4-yl)methyl 4-(1-hydroxy-1-methylethyl)-2-propyl-1-[2'-(1H-tetrazol-5-yl)biphenyl-4-ylmethyl]imidazole-5-carboxylate. The CS-866 of the present application includes its carboxylic acid derivative, pharmacologically acceptable esters of its carboxylic acid derivative (such as CS-866) and their pharmacologically acceptable salts.

Losartan (DUP-753) is described in Japanese Patent Application (Kokai) No. Sho 63-23868, U.S. Pat. No. 5,138,069 and the like, and its chemical name is 2-butyl-4-chloro-1-[2'-(1H-tetrazol-5-yl)biphenyl-4-ylmethyl]-1H-imidazole-5-methanol. The losartan of the present application includes its pharmacologically acceptable salts (such as losartan potassium salt).

Candesartan (TCV-116) is described in Japanese Patent Application (Kokai) No. Hei 4-364171, EP-459136, U.S. Pat. No. 5,354,766 and the like, and its chemical name is 1-(cyclohexyloxycarbonyloxy)ethyl 2-ethoxy-1-[2'-(1H-tetrazol-5-yl)biphenyl-4-ylmethyl]-1H-benzimidazole-7-carboxylate. The candesartan of the present application includes its carboxylic acid derivative, pharmacologically acceptable esters of its carboxylic acid derivative (such as TCV-116) and their pharmacologically acceptable salts.

Valsartan (CGP-48933) is described in Japanese Patent Application (Kokai) No. Hei 4-159718, EP-433983 and the like, and its chemical name is (S)-N-valeryl-N-[2'-(1H-tetrazol-5-yl)biphenyl-4-ylmethyl)valine. The valsartan of the present application includes its pharmacologically acceptable esters and its pharmacologically acceptable salts.

Irbesartan (SR-47436) is described in Japanese PCT Application (Kokai) No. Hei 4-506222, WO91-14679 and the like, and its chemical name is 2-N-butyl-4-spirocyclopentane-1-[2'-(tetrazol-5-yl)biphenyl-4-ylmethyl]-2-imidazolin-5-one. The irbesartan of the present application includes its pharmacologically acceptable salts.

In addition, where the above-mentioned compounds have asymmetric carbons, the angiotensin II receptor antagonists of the present invention also include optical isomers and mixtures of said isomers. Moreover, hydrates of the above-mentioned compounds are also included.

Representative examples of the angiotensin converting enzyme inhibitors as an active ingredient of the present invention include tetrahydrothiazepine compounds, proline compounds, pyridazinodiazepine compounds, glycine compounds, imidazolidine compounds and isoquinoline compounds described in Japanese Patent Application (Kokai) No. Sho 61-267579, Japanese Patent Application (Kokai) No. Sho 52-116457, U.S. Pat. No. 4,374,829, Japanese Patent Application (Kokai) No. Sho 58-126851, Japanese Patent Application (Kokai) No. Sho 58-206591, Japanese Patent Application (Kokai) No. Sho 57-77651, Japanese Patent Application (Kokai) No. Sho 55-9058, Japanese Patent Application (Kokai) No. Sho 58-203971 and Japanese Patent Application (Kokai) No. Sho 63-258459, preferably temocapril, captopril, enalapril, lisinopril, cilazapril, delapril, alacepril, imidapril or quinapril, more preferably temocapril, captopril or enalapril, and most preferably temocapril.

The following indicates the chemical planar structural formulae of some typical examples of angiotensin converting enzyme inhibitors.

Temocapril

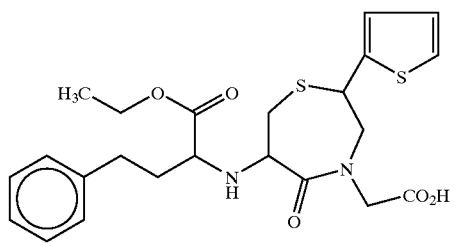

Captopril

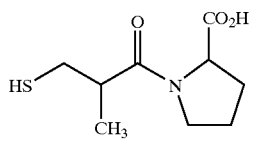

Enalapril

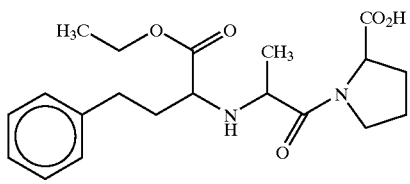

Lisinopril

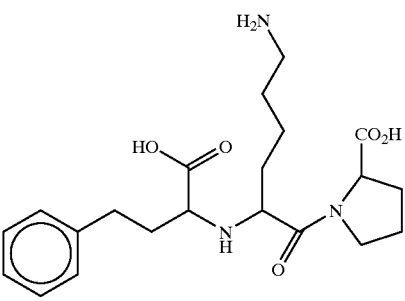

Cilazapril

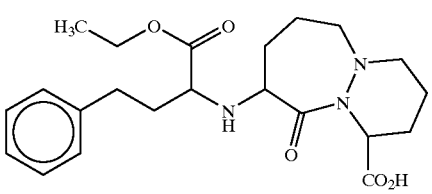

Delapril

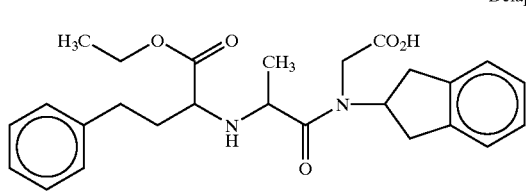

Alacepril

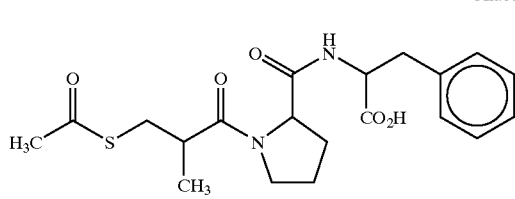

Imidapril

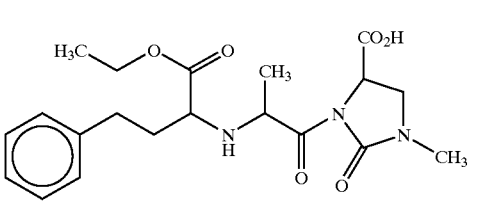

Quinapril

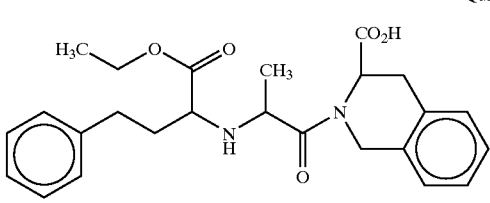

Temocapril is described in Japanese Patent Application (Kokai) No. Sho 61-267579, U.S. Pat. No. 4,699,905 and the like, and its chemical name is (+)-(2S,6R)-[6-(1S)-1-ethoxycarbonyl-3-phenylpropylamino]-5-oxo-2-(2-thienyl)perhydro-1,4-thiazepin-4-yl acetic acid. The temocapril of the present application includes its dicarboxylic acid derivatives, its pharmacologically acceptable salts, its pharmacologically acceptable monoesters and its pharmacologically acceptable salts (such as temocapril hydrochloride).

Captopril is described in Japanese Patent Application (Kokai) No. Sho 52-116457, U.S. Pat. No. 4,046,889 and the like, and its chemical name is 1-[(2S)-3-mercapto-2- methylpropionyl]-L-proline. The captopril of the present application includes its pharmacologically acceptable esters and its pharmacologically acceptable salts.

Enalapril is described in U.S. Pat. No. 4,374,829 and the like, and its chemical name is N-[(S)-1-ethoxycarbonyl-3-phenylpropyl]-L-alanyl-L-proline. The enalapril of the present application includes its pharmacologically acceptable esters and its pharmacologically acceptable salts (such as enalapril maleate).

Lisinopril is described in Japanese Patent Application (Kokai) No. Sho 58-126851, U.S. Pat. No. 4,555,502 and the like, and its chemical name is (S)-1-[$N^2$-(1-carboxy-3-phenylpropyl)-L-lysyl]-L-proline. The lisinopril of the present application includes its pharmacologically acceptable esters and its pharmacologically acceptable salts.

Cilazapril is described in Japanese Patent Application (Kokai) No. Sho 58-206591, U.S. Pat. No. 4,512,924 and the like, and its chemical name is (1S,9S)-9-[(S)-1-ethoxycarbonyl-3-phenylpropylamino]octahydro-10-oxo-6H-pyridazino[1,2-α][1,2]diazepine-1-carboxylic acid. The cilazapril of the present application includes its pharmacologically acceptable esters and pharmacologically acceptable salts.

Delapril is described in Japanese Patent Application (Kokai) No. Sho 57-77651, U.S. Pat. No. 4,385,051 and the like, and its chemical name is (S)-N-(2,3-dihydro-1H-inden-2-yl)-N-[N-(1-ethoxycarbonyl-3-phenylpropyl)-L-alanyl] glycine. The delapril of the present application includes its pharmacologically acceptable esters and its pharmacologically acceptable salts.

Alacepril is described in Japanese Patent Application (Kokai) No. Sho 55-9058, U.S. Pat. No. 4,248,883 and the like, and its chemical name is 1-(D-3-acetylthio-2-methylpropanoyl)-L-prolyl-L-phenylalanine. The alacepril of the present application includes its pharmacologically acceptable esters and its pharmacologically acceptable salts.

Imidapril is described in Japanese Patent Application (Kokai) No. Sho 58-203971, U.S. Pat. No. 4,508,727 and the like, and its chemical name is (4S)-3-[(2S)-2-[(1S)-1-ethoxycarbonyl-3-phenylpropylamino]propionyl]-1-methyl-2-oxoimidazolidine-4-carboxylic acid. The imidapril of the present application includes its pharmacologically acceptable esters and its pharmacologically acceptable salts.

Quinapril is described in Japanese Patent Application (Kokai) No. Sho 63-258459, U.S. Pat. No. 4,761,479 and the like, and its chemical name is (S)-2-[(2S)-2-(1S)-1-ethoxycarbonyl-3-phenylpropylamino)propionyl]-1,2,3,4-tetrahydro-3-isoquinoline carboxylic acid. The quinapril of the present application includes its pharmacologically acceptable esters and its pharmacologically acceptable salts.

Where the above-mentioned angiotensin converting enzyme inhibitors of the present invention have asymmetric carbons, said angiotensin converting enzyme inhibitors of the present invention also include their optical isomers and mixtures of said isomers. Moreover, hydrates of the above-mentioned compounds are also included in the present invention.

The insulin resistance improving agents as another active ingredient of the present invention are inherently used for the prevention and treatment of diabetes. Representative examples include thiazolidinedione compounds, oxazolidinedione compounds or oxadiazolidinedione compounds described in Japanese Patent Application (Kokai) No. Hei 4-69383, WO 89/08651, WO 91/07107, WO 92/02520, WO 94/01433, U.S. Pat. No. 4,287,200, U.S. Pat. No. 4,340,605, U.S. Pat. No. 4,438,141, U.S. Pat. No. 4,444,779, U.S. Pat. No. 4,461,902, U.S. Pat. No. 4,572,912, U.S. Pat. No. 4,687,777, U.S. Pat. No. 4,703,052, U.S. Pat. No. 4,725,610, U.S. Pat. No. 4,873,255, U.S. Pat. No. 4,897,393, U.S. Pat. No. 4,897,405, U.S. Pat. No. 4,918,091, U.S. Pat. No. 4,948,900, U.S. Pat. No. 5,002,953, U.S. Pat. No. 5,061,717, U.S. Pat. No. 5,120,754, U.S. Pat. No. 5,132,317, U.S. Pat. No. 5,194,443, U.S. Pat. No. 5,223,522, U.S. Pat. No. 5,232,925 and U.S. Pat. No. 5,260,445, preferably thiazolidinedione compounds, more preferably troglitazone, pioglitazone, englitazone or BRL-49653, still more preferably troglitazone or pioglitazone, and most preferably troglitazone.

The following indicates the chemical planar structural formulae of some typical examples of insulin resistance improving agents.

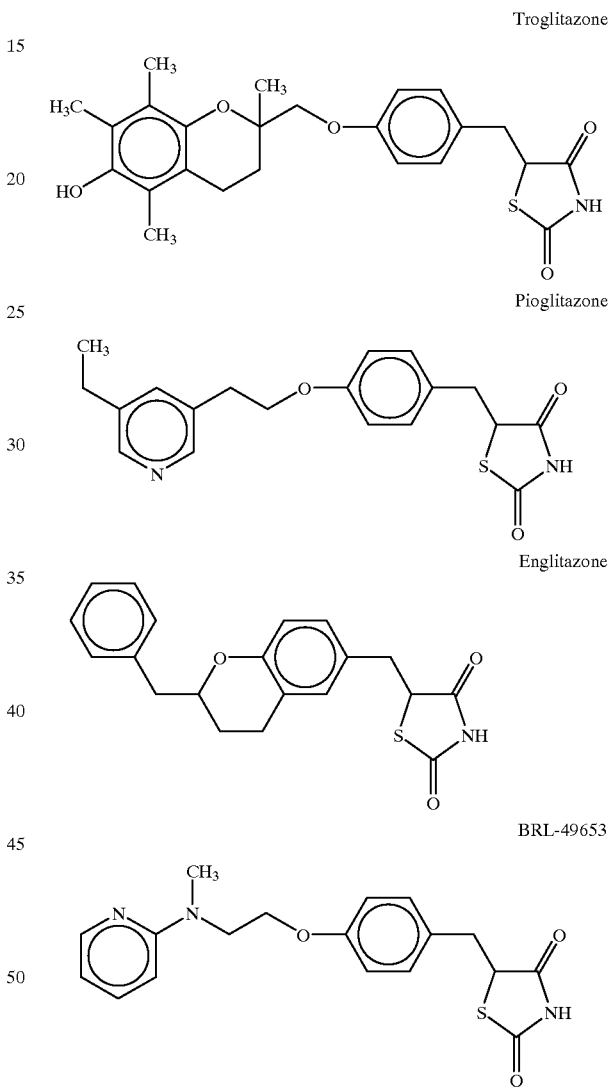

Troglitazone is described in Japanese Patent Application (Kokai) No. Sho 60-51189, U.S. Pat. No. 4,572,912 and the like, and its chemical name is 5-[4-(6-hydroxy-2,5,7,8-tetramethylchroman-2-ylmethoxy)benzyl]-2,4-thiazolidinedione. The troglitazone of the present application includes its pharmacologically acceptable salts.

Pioglitazone is described in Japanese Patent Application (Kokai) No. Sho 55-22636, U.S. Pat. No. 4,287,200 and the like, and its chemical name is 5-[4-[2-(5-ethyl-pyridin-2-yl) ethoxy]phenylmethyl]-2,4-thiazolidinedione. The pioglitazone of the present application includes its pharmacologically acceptable salts.

Englitazone is described in Japanese Patent Application (Kokai) No. Sho 61-271287, U.S. Pat. No. 4,703,052 and the like, and its chemical name is 5-(3,4-dihydro-2-benzyl-2H-benzopyran-6-ylmethyl)-2,4-thiazolidinedione. The englitazone of the present application includes its pharmacologically acceptable salts.

BRL49653 is described in Japanese Patent Application (Kokai) No. Hei 1-131169, U.S. Pat. No. 5,002,953 and the like, and its chemical name is 5-[4-[2-[N-methyl-N-(pyridin-2-yl)amino]ethoxy]phenylmethyl]-2,4-thiazolidinedione. The BRL-49653 of the present application includes its pharmacologically acceptable salts.

Where the above-mentioned insulin resistance improving agents of the present invention have asymmetric carbons, said resistance improving agents the present invention also include their optical isomers and mixtures of said isomers. Moreover, hydrates of the above-mentioned compounds are also included in the present invention.

In the present invention, one or more drugs are selected from the group consisting of angiotensin II receptor antagonists and angiotensin converting enzyme inhibitors (preferably the group consisting of angiotensin II receptor antagonists), and one or more insulin resistance improving agents are selected; and preferably the one drug is selected from angiotensin II receptor antagonists and angiotensin converting enzyme inhibitors and the other drug is selected from insulin resistance improving agents to use in combination.

Preferable examples of the pharmaceutical composition of the present invention are as follows:

(1) a pharmaceutical composition wherein as active ingredients, the angiotensin II receptor antagonists are chosen from biphenyltetrazole compounds and biphenylcarboxylic acid compounds and the angiotensin converting enzyme inhibitors are chosen from tetrahydrothiazepine compounds, proline compounds, pyridazinodiazepine compounds, glycine compounds, imidazolidine compounds and isoquinoline compounds;

(2) a pharmaceutical composition wherein as active ingredients, the drugs consisting of angiotensin II receptor antagonists and angiotensin converting enzyme inhibitors are chosen from CS-866, losartan, candesartan, valsartan, irbesartan, temocapril, captopril, enalapril, lisinopril, cilazapril, delapril, alacepril, imidapril and quinapril;

(3) a pharmaceutical composition wherein as active ingredients, the drugs consisting of angiotensin II receptor antagonists and angiotensin converting enzyme inhibitors are chosen from CS-866, losartan, candesartan, valsartan, irbesartan, temocapril, captopril and enalapril;

(4) a pharmaceutical composition wherein as active ingredients, the drugs consisting of angiotensin II receptor antagonists and angiotensin converting enzyme inhibitors are chosen from CS-866, losartan, candesartan and temocapril;

(5) a pharmaceutical composition wherein as active ingredients, the drugs consisting of angiotensin II receptor antagonists and angiotensin converting enzyme inhibitors are chosen from CS-866, losartan and candesartan;

(6) a pharmaceutical composition wherein as an active ingredient, the drug consisting of angiotensin II receptor antagonists and angiotensin converting enzyme inhibitors is CS-866;

(7) a pharmaceutical composition wherein as active ingredients, the drugs consisting of angiotensin II receptor antagonists and angiotensin converting enzyme inhibitors are angiotensin II receptor antagonists;

(8) a pharmaceutical composition wherein as active ingredients, the drugs consisting of angiotensin II receptor antagonists and angiotensin converting enzyme inhibitors are chosen from CS-866, losartan, candesartan, valsartan and irbesartan;

(9) a pharmaceutical composition wherein as active ingredients, the drugs consisting of angiotensin II receptor antagonists and angiotensin converting enzyme inhibitors are chosen from angiotensin converting enzyme inhibitors;

(10) a pharmaceutical composition wherein as an active ingredient, the drug consisting of angiotensin II receptor antagonists and angiotensin converting enzyme inhibitor is temocapril;

(11) a pharmaceutical composition wherein as active ingredients, the insulin resistance improving agents are chosen from thiazolidinedione compounds, oxazolidinedione compounds and oxadiazolidinedione compounds;

(12) a pharmaceutical composition wherein as active ingredients, the insulin resistance improving agents are chosen from troglitazone, pioglitazone, englitazone and BRL49653;

(13) a pharmaceutical composition wherein as active ingredients, the insulin resistance improving agents are chosen from troglitazone and pioglitazone; and,

(14) a pharmaceutical composition wherein as an active ingredient, the insulin resistance improving agent is troglitazone.

In addition, a pharmaceutical composition obtained by selecting as active ingredients, the drugs consisting of angiotensin II receptor antagonists and angiotensin converting enzyme inhibitors from the group (1) to (10), by selecting as active ingredients, insulin resistance improving agents from the group (11) to (14) and by combining these groups in an arbitrary manner is also preferable, examples of which are as follows:

(15) a pharmaceutical composition wherein as active ingredients, the drugs consisting of angiotensin II receptor antagonists and angiotensin converting enzyme inhibitors are chosen from CS-866, losartan, candesartan, valsartan, irbesartan, temocapril, captopril, enalapril, lisinopril, cilazapril, delapril, alacepril, imidapril and quinapril, and as the other active ingredient, the insulin resistance improving agents are chosen from troglitazone, pioglitazone, englitazone and BRL-49653;

(16) a pharmaceutical composition wherein as active ingredients, the drugs consisting of angiotensin II receptor antagonists and angiotensin converting enzyme inhibitors are chosen from CS-866, losartan, candesartan, valsartan, irbesartan, temocapril, captopril and enalapril, and as the other active ingredient, the insulin resistance improving agents are chosen from troglitazone, pioglitazone, englitazone and BRL49653;

(17) a pharmaceutical composition wherein as active ingredients, the drugs consisting of angiotensin II receptor antagonists and angiotensin converting enzyme inhibitors are chosen from CS-866, losartan, candesartan and temocapril, and as the other active ingredient, the insulin resistance improving agents are chosen from troglitazone and pioglitazone;

(18) a pharmaceutical composition wherein as active ingredients, the drugs consisting of angiotensin II receptor antagonists and angiotensin converting enzyme inhibitors are chosen from CS-866, losartan and candesartan, and as the other active ingredient, the insulin resistance improving agents are chosen from troglitazone and pioglitazone;

(19) a pharmaceutical composition wherein as an active ingredient, the drug consisting of angiotensin II receptor antagonists and angiotensin converting enzyme inhibitors is CS-866, and as the other active ingredient, the insulin resistance improving agents are chosen from troglitazone and pioglitazone;

(20) a pharmaceutical composition wherein as active ingredients, the drugs consisting of angiotensin II receptor antagonists and angiotensin converting enzyme inhibitors are chosen from CS-866, losartan and candesartan, and as the other active ingredient, the insulin resistance improving agent is troglitazone;

(21) a pharmaceutical composition wherein as an active ingredient, the drug consisting of angiotensin II receptor antagonists and angiotensin converting enzyme inhibitors is CS-866, and as the other active ingredient, the insulin resistance improving agent is troglitazone; and,

(22) a pharmaceutical composition wherein as an active ingredient, the drug consisting of angiotensin II receptor antagonists and angiotensin converting enzyme inhibitors is temocapril, and as the other active ingredient, the insulin resistance improving agent is troglitazone.

A drug comprising one or more drugs selected from the group consisting of angiotensin II receptor antagonists and angiotensin converting enzyme inhibitors, and one or more insulin resistance improving agents, which are the active ingredients of the pharmaceutical composition of the present invention (particularly a composition for prevention or treatment of arteriosclerosis), has excellent inhibitory action on aortosclerosis and excellent inhibitory action against onset of xanthochromia occurring in limb joints, and low toxicity. Consequently, it is useful as a drug for the prevention and treatment (particularly for treatment) of arteriosclerosis or xanthochromia in humans.

According to the present invention, drugs consisting of angiotensin II receptor antagonists and angiotensin converting enzyme inhibitors and insulin resistance improving agents exhibit excellent effects by using two of these agents in combination as compared with being used alone. In addition, these effects can be achieved without requiring that both types of agents be present in the body simultaneously.

Namely, such effects can be obtained even if both types of agents do not simultaneously have certain concentrations in the blood. According to hypothesis, if two types of agents used in the present invention are both incorporated in vivo and reach the receptors, they have the effect of turning on a switch in vivo. Thus, even if it appears that such effects are not demonstrated at their blood concentrations in course of time after their administration, the switch is actually still on, thereby allowing demonstration of preventive or therapeutic effects on arterial sclerosis possessed by the one type of substance. When the other type of agent is administered in this state, in addition to the preventive or therapeutic effects on arterial sclerosis possessed by that agent, the effects of the drug initially administered are combined to obtain excellent effects. Naturally, since it is convenient clinically to administer two types of agents simultaneously, drugs consisting of angiotensin II receptor antagonists and angiotensin converting enzyme inhibitors and an insulin resistance improving agent can be administered in the form of a combination drug. In cases where it is undesirable to physically mix both agents simultaneously in consideration of pharmaceutical formulation technology, each individual agent may be administered simultaneously. In addition, as was stated above, since excellent effects are demonstrated even if the two types of agents are not administered simultaneously, each individual agent can also be administered at a suitable interval in succession. The maximum administration interval of the two types of agents to demonstrate the excellent effects brought about by said two types of agents can be determined by clinical or animal studies.

The administration route of the drugs consisting of angiotensin II receptor antagonists and angiotensin converting enzyme inhibitors, and of the insulin resistance improving agents used in the present invention is typically the oral administration route. Thus, the two types of agents can either be prepared in the form of two separate administrations or in the form of a single administration by physically mixing the two types of agents. The administration form can be, for example, a powder, granules, tablet or capsule and the like, and can be prepared by using conventional pharmaceutical formulation techniques.

The dose and administration ratio of the drugs consisting of angiotensin II receptor antagonists and angiotensin converting enzyme inhibitors, and of the insulin resistance improving agents used in the present invention can be changed over a wide range according to various conditions such as the individual activity of each agent, the patient's symptoms, age and body weight, and the like. For example, in the case of insulin resistance improving agents, since the in vivo activities of troglitazone and BRL49653 by using a diabetic animal model are different, the dose of these two agents may be different by a factor of ten or more. In addition, for both agents consisting of angiotensin II receptor antagonists and angiotensin converting enzyme inhibitors, and insulin resistance improving agents, their doses in the case used for prevention or treatment of arteriosclerosis in the present invention can be lower than their dose for use as hypotensive agents and diabetes therapeutic agents respectively, which are their well-known applications. In addition, their doses can be made even lower due to the excellent effects resulting from combined use of both types of agents. For example, in the case of using CS-866 and troglitazone for the object of the present invention, their doses are lower than the approximately 5 to 100 mg and approximately 10 to 2000 mg, respectively, which are the doses for adults (mg/day) for use as a hypotensive agent and diabetes therapeutic agent in their well-known applications, being able to be approximately 1 to 80 mg and approximately 1 to 1000 mg, respectively.

As has been described above, the doses of the drugs consisting of angiotensin II receptor antagonists and angiotensin converting enzyme inhibitors and of the insulin resistance improving agents can be varied over a wide range, in general, and their doses for adults (mg/day) are approximately 0.5 to 100 mg and approximately 0.05 to 1,500 mg, respectively.

The ratio of the doses of these two types of agents can also be varied over a wide range, in general, and the dose ratio of the drugs consisting of angiotensin II receptor antagonists and angiotensin converting enzyme inhibitors to the insulin resistance improving agents can be, in terms of weight ratio, within the range from 1:200 to 200:1.

In the present invention, the drugs consisting of angiotensin II receptor antagonists and angiotensin converting enzyme inhibitors, and the insulin resistance improving agents are administered at the respective doses described above once a day or divided among several times per day, and may be administered simultaneously or separately at respectively different times.

The present invention will be described more specifically by way of Examples and Preparation examples, but the scope of the present invention is not limited to them.

EXAMPLE 1

Arterial Sclerosis Progress Inhibitory Effect

A certain amount of an agent was administered orally for 32 weeks to 2–3 months old WHHL rabbits, Watanabe genetically hyperlipemic rabbits: supra (Biochimica et Biophysica Acta), etc., in groups of 4 to 7 animals each. Incidentally, food consumption was restricted to 120 g/day per animal. Blood samples were collected immediately before administration of the agent and 4, 8, 12, 16, 20, 24, 28 and 32 weeks after the start of administration to measure total cholesterol levels (mg/dl). There were no changes observed in any of the dose groups as compared with the control group to which no agents were administered. The test animals were subjected to autopsy in the 32nd week to investigate the surface area of aortic lesions (%) and the incidence of xanthochromia in finger joints (%). Those results are shown in Tables 1 and 2.

TABLE 1

Surface Area of Aortic Lesions

| Test No. | Test Compound | Dose (mg/kg) | No. of animals | Arcuate region | Thoracic part | Abdominal region | Overall |
|---|---|---|---|---|---|---|---|
| 1 | CS-866 + Troglitazone | 1 25 | 5 | 52 ± 10 | 9 ± 3 | 13 ± 2 | 21 ± 4 |
|  | CS-866 | 1 | 6 | 68 ± 10 | 26 ± 8 | 19 ± 5 | 34 ± 7 |
|  | Troglitazone | 25 | 7 | 80 ± 7 | 57 ± 12 | 32 ± 8 | 54 ± 9 |
|  | Control | — | 7 | 83 ± 6 | 59 ± 7 | 39 ± 4 | 56 ± 4 |

TABLE 2

Incidence of Xanthochromia in Finger Joints

| Test No. | Test Compound | Dose (mg/kg) | No. of animals | Fore-limbs | Hind-limbs | Overall |
|---|---|---|---|---|---|---|
| 1 | CS-866 + Troglitazone | 1 25 | 4 | 75 | 63 | 69 |
|  | CS-866 | 1 | 6 | 100 | 100 | 100 |
|  | Troglitazone | 25 | 7 | 93 | 86 | 89 |
|  | Control | — | 7 | 100 | 100 | 100 |

EXAMPLE 2

Arterial Sclerosis Progress Inhibitory Effect

A certain amount of an agent was administered orally for 31 weeks to 2–3 months old WHHL rabbits, Watanabe genetically hyperlipemic rabbits: described supra (Biochimica et Biophysica Acta), etc., in groups of 5 to 7 animals each. Incidentally, food consumption was restricted to 100 g/day per animal. Blood samples were collected immediately before administration of the agent and 8, 16, 24 and 31 weeks after the start of administration to measure total cholesterol levels (mg/dl). There were no changes observed in any of the dose groups as compared with the control group to which no agents were administered. In addition, the test animals were subjected to autopsy in the 31st week to investigate the surface area of aortic lesions (%) and the incidence of xanthochromia in finger joints. Those results are shown in Tables 3 and 4.

TABLE 3

Surface Area of Aortic Lesions

| Test No. | Test Compound | Dose (mg/kg) | No. of animals | Arcuate region | Thoracic part | Abdominal region | Overall |
|---|---|---|---|---|---|---|---|
| 2 | CS-866 + pioglitazone | 0.5 20 | 6 | 62 ± 8 | 29 ± 10 | 24 ± 6 | 36 ± 7 |
| 3 | CS-866 + BRL-49653 | 0.5 2.5 | 5 | 52 ± 5 | 32 ± 7 | 25 ± 5 | 34 ± 5 |
|  | CS-866 | 0.5 | 7 | 66 ± 5 | 41 ± 10 | 32 ± 8 | 44 ± 7 |
|  | Pioglitazone | 20 | 7 | 65 ± 6 | 62 ± 12 | 32 ± 6 | 52 ± 8 |
|  | BRL-49653 | 2.5 | 6 | 83 ± 2 | 54 ± 12 | 29 ± 4 | 52 ± 5 |
|  | Control | — | 7 | 84 ± 5 | 59 ± 9 | 32 ± 11 | 54 ± 8 |

TABLE 4

Incidence of Xanthochromia in Finger Joints

| Test No. | Test Compound | Dose (mg/kg) | No. of animals | Fore-limbs | Hind-limbs | Overall |
|---|---|---|---|---|---|---|
| 4 | Candesartan + troglitazone | 1 25 | 7 | 86 | 86 | 86 |
|  | Candesartan | 1 | 7 | 100 | 100 | 100 |
|  | Troglitazone | 25 | 7 | 100 | 86 | 93 |
|  | Control | — | 7 | 100 | 100 | 100 |

FORMULATION EXAMPLE 1

| Tablets | |
|---|---|
| CS-866 | 4.0 mg |
| Troglitazone | 100.0 |
| Lactose | 244.0 |
| Cornstarch | 50.0 |
| Magnesium stearate | 2.0 |
| | 400 mg |

The above-mentioned prescriptions are mixed and formed into tablets with a tablet-making machine to obtain tablets containing 400 mg per tablet.

These tablets can be provided with a sugar-coating if necessary.

A kit of the present invention is illustrated by a kit including a first container (or a plurality of first containers) which contain a pharmaceutical composition comprising CS-866 and a second container (or a plurality of second containers) which contain a pharmaceutical composition comprising troglitazone.

We claim:

1. A pharmaceutical composition for the treatment of arteriosclerosis comprising a pharmaceutically effective amount of a combination of (a) at least one drug selected from the group consisting of an insulin resistance improving agent or a pharmacologically acceptable salt thereof with (b) at least one drug selected from the group consisting of (i) an angiotensin II receptor antagonist or a pharmacologically acceptable salt thereof and (ii) an angiotensin converting enzyme inhibitor or a pharmacologically acceptable salt thereof, together with a pharmaceutically acceptable diluent or carrier therefor.

2. The pharmaceutical composition according to claim 1, wherein said (b) comprises at least one drug selected from the group consisting of (i) an angiotensin II receptor antagonist selected from the group consisting of a biphenyl tetrazole compound and a biphenylcarboxylic acid compound, and (ii) an angiotensin converting enzyme inhibitor selected from the group consisting of a tetrahydrothiazepine compound, a proline compound, a pyridazinodiazepine compound, a glycine compound, an imidazolidine compound and an isoquinoline compound.

3. The pharmaceutical composition according to claim 1, wherein said (b) selected from the group consisting of (i) an angiotensin II receptor antagonist and (ii) an angiotensin converting enzyme inhibitor comprises at least one compound selected from the group consisting of CS-866, losartan, candesartan, valsartan, irbesartan, temocapril, captopril, enalapril, lisinopril, cilazapril, delapril, alacepril, imidapril and quinapril.

4. The pharmaceutical composition according to claim 1, wherein said (b) selected from the group consisting of (i) an angiotensin II receptor antagonist and (ii) an angiotensin converting enzyme inhibitor comprises at least one compound selected from the group consisting of CS-866, losartan, candesartan, valsartan, irbesartan, temocapril, captopril and enalapril.

5. The pharmaceutical composition according to claim 1, wherein said (b) selected from the group consisting of (i) an angiotensin II receptor antagonist and (ii) an angiotensin converting enzyme inhibitor comprises at least one compound selected from the group consisting of CS-866, losartan, candesartan and temocapril.

6. The pharmaceutical composition according to claim 1, wherein said (b) selected from the group consisting of (i) an angiotensin II receptor antagonist and (ii) an angiotensin converting enzyme inhibitor comprises at least one compound selected from the group consisting of CS-866, losartan and candesartan.

7. The pharmaceutical composition according to claim 1, wherein said drug selected from the group consisting of (i) an angiotensin II receptor antagonist and (ii) an angiotensin converting enzyme inhibitor is CS-866.

8. The pharmaceutical composition according to claim 1, wherein one or more drugs selected from said group consisting of insulin resistance improving agents are in combination with one or more drugs selected from the group consisting of angiotensin II receptor antagonists.

9. The pharmaceutical composition according to claim 1, wherein one or more drugs selected from said group consisting of insulin resistance improving agents are in combination with one or more drugs selected from the group consisting of the angiotensin II receptor antagonists CS-866, losartan, candesartan, valsartan and irbesartan.

10. The pharmaceutical composition according to claim 1, wherein one or more drugs selected from said group consisting of insulin resistance improving agents are in combination with one or more drugs selected from the group consisting of angiotensin converting enzyme inhibitors.

11. The pharmaceutical composition according to claim 1, wherein one or more drugs selected from said group consisting of insulin resistance improving agents are in combination with the angiotensin converting enzyme inhibitor temocapril.

12. The pharmaceutical composition according to claim 1, wherein said insulin resistance improving agents are selected from the group consisting of thiazolidinedione compounds, oxazolidinedione compounds and oxadiazolidinedione compounds.

13. The pharmaceutical composition according to claim 1, wherein said insulin resistance improving agent is pioglitazone.

14. The pharmaceutical composition according to claim 1, wherein said insulin resistance improving agents are selected from the group consisting of troglitazone and pioglitazone.

15. The pharmaceutical composition according to claim 1, wherein said insulin resistance improving agent is troglitazone.

16. The pharmaceutical composition according to claim 1, wherein said angiotensin II receptor antagonists and angiotensin converting enzyme inhibitors are selected from the group consisting of CS-866, losartan, candesartan, valsartan, irbesartan, temocapril, captopril, enalapril, lisinopril, cilazapril, delapril, alacepril, imidapril and quinapril, and said insulin resistance improving agents are selected from the group consisting of troglitazone, pioglitazone, englitazone and BRL-49653.

17. The pharmaceutical composition according to claim 1, wherein said angiotensin II receptor antagonists and angiotensin converting enzyme inhibitors are selected from the group consisting of CS-866, losartan, candesartan, valsartan, irbesartan, temocapril, captopril and enalapril, and said insulin resistance improving agents are selected from the group consisting of troglitazone, pioglitazone, englitazone and BRL-49653.

18. The pharmaceutical composition according to claim 1, wherein said angiotensin II receptor antagonists and angiotensin converting enzyme inhibitors are selected from the group consisting of CS-866, losartan, candesartan and temocapril, and said insulin resistance improving agents are selected from the group consisting of troglitazone and pioglitazone.

19. The pharmaceutical composition according to claim 1, wherein said angiotensin II receptor antagonists and angiotensin converting enzyme inhibitors are selected from the group consisting of CS-866, losartan and candesartan, and said insulin resistance improving agents are selected from the group consisting of troglitazone and pioglitazone.

20. The pharmaceutical composition according to claim 1, wherein insulin resistance improving agents selected from the group consisting of troglitazone and pioglitazone are in combination with the angiotensin II receptor antagonist CS-866.

21. The pharmaceutical composition according to claim 1, wherein said (b) comprises at least one angiotensin II receptor antagonist selected from the group consisting of CS-866, losartan and candesartan; and the insulin resistance improving agent is troglitazone.

22. The pharmaceutical composition according to claim 1, wherein said (b) is the angiotensin II receptor antagonist CS-866; and the insulin resistance improving agent is troglitazone.

23. The pharmaceutical composition according to claim 1, wherein said (b) is the angiotensin converting enzyme inhibitor temocapril; and the insulin resistance improving agent is troglitazone.

24. The pharmaceutical composition according to claim 1, wherein the amount of said (a) to the amount of said (b) is in a weight ratio of 1:200 to 200:1.

25. The pharmaceutical composition according to claim 1, wherein said insulin resistance improvement agent is englitazone.

26. The pharmaceutical composition according to claim 1, wherein said insulin resistance improvement agent is BRL-49653.

27. A kit comprising a plurality of containers, the contents of at least two containers differing from each other in whole or in part, in which at least one of said containers contains (a) at least one drug selected from the group consisting of insulin resistance improving agents or a pharmacologically acceptable salt thereof, and at least one different container contains (b) at least one drug selected from the group consisting of (i) an angiotensin II receptor antagonist or a pharmacologically acceptable salt thereof and (ii) an angiotensin converting enzyme inhibitor or a pharmacologically acceptable salt thereof, the contents of the containers in total comprising a pharmaceutically effective amount of a combination of said (a) and said (b).

28. The kit according to claim 27, wherein said (b) comprises at least one drug selected from the group consisting of (i) an angiotensin II receptor antagonist selected from the group consisting of a biphenyl tetrazole compound and a biphenylcarboxylic acid compound, and (ii) an angiotensin converting enzyme inhibitor selected from the group consisting of a tetrahydrothiazepine compound, a praline compound, a pyridazinodiazepine compound, a glycine compound, an imidazolidine compound and an isoquinoline compound.

29. The kit according to claim 27, wherein said (b) selected from the group consisting of (i) an angiotensin II receptor antagonist and (ii) an angiotensin converting enzyme inhibitor comprises at least one compound selected from the group consisting of CS-866, losartan, candesartan, valsartan, irbesartan, temocapril, captopril, enalapril, lisinopril, cilazapril, delapril, alacepril, imidapril and quinapril.

30. The kit according to claim 27, wherein said (b) selected from the group consisting of (i) an angiotensin II receptor antagonist and (ii) an angiotensin converting enzyme inhibitor comprises at least one compound selected from the group consisting of CS-866, losartan, candesartan, valsartan, irbesartan, temocapril, captopril and enalapril.

31. The kit according to claim 27, wherein said (b) selected from the group consisting of (i) an angiotensin II receptor antagonist and (ii) an angiotensin converting enzyme inhibitor comprises at least one compound selected from the group consisting of CS-866, losartan, candesartan and temocapril.

32. The kit according to claim 27, wherein said (b) selected from the group consisting of (i) an angiotensin II receptor antagonist and (ii) an angiotensin converting enzyme inhibitor comprises at least one compound selected from the group consisting of CS-866, losartan and candesartan.

33. The kit according to claim 27, wherein the drug selected from the group consisting of angiotensin II receptor antagonists and angiotensin converting enzyme inhibitors is CS-866.

34. The kit according to claim 27, in which at least one of said containers contains at least one drug selected from the group consisting of insulin resistance improving agents and at least one different container contains at least one drug selected from the group consisting of angiotensin II receptor antagonists.

35. The kit according to claim 27, in which at least one of said containers contains at least one drug selected from the group consisting of insulin resistance improving agents and at least one different container contains at least one drug selected from the group consisting of the angiotensin II receptor antagonists CS-866, losartan, candesartan, valsartan and irbesartan.

36. The kit according to claim 27, in which at least one of said containers contains at least one drug selected from the group consisting of insulin resistance improving agents and at least one different container contains at least one drug selected from the group consisting of angiotensin converting enzyme inhibitors.

37. The kit according to claim 27, in which at least one of said containers contains at least one drug selected from the group consisting of insulin resistance improving agents and at least one different container contains the angiotensin converting enzyme inhibitor temocapril.

38. The kit according to claim 27, wherein said insulin resistance improving agents are selected from the group consisting of thiazolidinedione compounds, oxazolidinedione compounds and oxadiazolidinedione compounds.

39. The kit according to claim 27, wherein said insulin resistance improving agents are selected from the group consisting of troglitazone, pioglitazone, englitazone and BRL-49653.

40. The kit according to claim 27, wherein said insulin resistance improving agents are selected from the group consisting of troglitazone and pioglitazone.

41. The kit according to claim 27, wherein said insulin resistance improving agent is troglitazone.

42. The kit according to claim 27, wherein said angiotensin II receptor antagonists and angiotensin converting enzyme inhibitors are selected from the group consisting of CS-866, losartan, candesartan, valsartan, irbesartan, temocapril, captopril, enalapril, lisinopril, cilazapril, delapril, alacepril, imidapril and quinapril, and said insulin resistance improving agents are selected from the group consisting of troglitazone, pioglitazone, englitazone and BRL-49653.

43. The kit according to claim 27, wherein said angiotensin II receptor antagonists and angiotensin converting enzyme inhibitors are selected from the group consisting of CS-866, losartan, candesartan, valsartan, irbesartan, temocapril, captopril and enalapril, and said insulin resistance improving agents are selected from the group consisting of troglitazone, pioglitazone, englitazone and BRL-49653.

44. The kit according to claim 27, wherein said angiotensin II receptor antagonists and angiotensin converting enzyme inhibitors are selected from the group consisting of CS-866, losartan, candesartan and temocapril, and said insulin resistance improving agents are selected from the group consisting of troglitazone and pioglitazone.

45. The kit according to claim 27, wherein said angiotensin II receptor antagonists and angiotensin converting enzyme inhibitors are selected from the group consisting of CS-866, losartan and candesartan, and said insulin resistance improving agents are selected from the group consisting of troglitazone and pioglitazone.

46. The kit according to claim 27, wherein at least one container contains at least one drug selected from the group consisting of the insulin resistance improving agents troglitazone and pioglitazone and at least one different container contains the angiotensin II receptor antagonist CS-866.

47. The kit according to claim 27, wherein at least one container contains at least one drug selected from the group consisting of the angiotensin II receptor antagonists CS-866, losartan and candesartan and at least one different container contains the insulin resistance improving agent troglitazone.

48. The kit according to claim 27, wherein at least one container contains the angiotensin II receptor antagonist CS-866 and at least one different container contains the insulin resistance improving agent troglitazone.

49. The kit according to claim 27, wherein at least one container contains the angiotensin converting enzyme inhibitor temocapril and at least one different container contains the insulin resistance improving agent troglitazone.

50. The kit according to claim 27, wherein the amount of said (a) to the amount of said (b) is in a weight ratio of 1:200 to 200:1.

51. A method for the treatment of arteriosclerosis, which method comprises administering a pharmaceutically effective amount of a combination of (a) at least one drug selected from the group consisting of an insulin resistance improving agent or a pharmacologically acceptable salt thereof and (b) at least one drug selected from the group consisting of (i) an angiotensin II receptor antagonist or a pharmacologically acceptable salt thereof and (ii) an angiotensin converting enzyme inhibitor or a pharmacologically acceptable salt thereof to a mammal suffering from arteriosclerosis.

52. The method according to claim 51, wherein said (b) comprises at least one drug selected from the group consisting of (i) an angiotensin II receptor antagonist selected from the group consisting of a biphenyl tetrazole compound and a biphenylcarboxylic acid compound, and (ii) an angiotensin converting enzyme inhibitor selected from the group consisting of a tetrahydrothiazepine compound, a proline compound, a pyridazinodiazepine compound, a glycine compound, an imidazolidine compound and an isoquinoline compound.

53. The method according to claim 51, wherein said (b) selected from the group consisting of (i) an angiotensin II receptor antagonist and (ii) an angiotensin converting enzyme inhibitor comprises at least one compound selected from the group consisting of CS-866, losartan, candesartan, valsartan, irbesartan, temocapril, captopril, enalapril, lisinopril, cilazapril, delapril, alacepril, imidapril and quinapril.

54. The method according to claim 51, wherein said (b) selected from the group consisting of (i) an angiotensin II receptor antagonist and (ii) an angiotensin converting enzyme inhibitor comprises at least one compound selected from the group consisting of CS-866, losartan, candesartan, valsartan, irbesartan, temocapril, captopril and enalapril.

55. The method according to claim 51, wherein said (b) selected from the group consisting of (i) an angiotensin II receptor antagonist and (ii) an angiotensin converting enzyme inhibitor comprises at least one compound selected from the group consisting of CS-866, losartan, candesartan and temocapril.

56. The method according to claim 51, wherein said (b) selected from the group consisting of (i) an angiotensin II receptor antagonist and (ii) an angiotensin converting enzyme inhibitor comprises at least one compound selected from the group consisting of CS-866, losartan and candesartan.

57. The method according to claim 51, wherein said drug selected from the group consisting of (i) an angiotensin II receptor antagonist and (ii) an angiotensin converting enzyme inhibitor is CS-866.

58. The method according to claim 51, wherein one or more drugs selected from said group consisting of insulin resistance improving agents are administered in combination with one or more drugs selected from the group consisting of angiotensin II receptor antagonists.

59. The method according to claim 51, wherein one or more drugs selected from said group consisting of insulin resistance improving agents are administered in combination with one or more drugs selected from the group consisting of the angiotensin II receptor antagonists CS-866, losartan, candesartan, valsartan and irbesartan.

60. The method according to claim 51, wherein one or more drugs selected from said group consisting of insulin resistance improving agents are administered in combination with one or more drugs selected from the group consisting of angiotensin converting enzyme inhibitors.

61. The method according to claim 51, wherein one or more drugs selected from said group consisting of insulin resistance improving agents are administered in combination with the angiotensin converting enzyme inhibitor temocapril.

62. The method according to claim 51, wherein said insulin resistance improving agents are selected from the group consisting of thiazolidinedione compounds, oxazolidinedione compounds and oxadiazolidinedione compounds.

63. The method according to claim 51, wherein said insulin resistance improving agent is pioglitazone.

64. The method according to claim 51, wherein said insulin resistance improving agents are selected from the group consisting of troglitazone and pioglitazone.

65. The method according to claim 51, wherein said insulin resistance improving agent is troglitazone.

66. The method according to claim 51, wherein said angiotensin II receptor antagonists and angiotensin converting enzyme inhibitors are selected from the group consisting of CS-866, losartan, candesartan, valsartan, irbesartan, temocapril, captopril, enalapril, lisinopril, cilazapril, delapril, alacepril, imidapril and quinapril, and said insulin resistance improving agents are selected from the group consisting of troglitazone, pioglitazone, englitazone and BRL-49653.

67. The method according to claim 51, wherein said angiotensin II receptor antagonists and angiotensin converting enzyme inhibitors are selected from the group consisting of CS-866, losartan, candesartan, valsartan, irbesartan, temocapril, captopril and enalapril, and said insulin resistance improving agents are selected from the group consisting of troglitazone, pioglitazone, englitazone and BRL-49653.

68. The method according to claim 51, wherein said angiotensin II receptor antagonists and angiotensin converting enzyme inhibitors are selected from the group consisting of CS-866, losartan, candesartan and temocapril, and said insulin resistance improving agents are selected from the group consisting of troglitazone and pioglitazone.

69. The method according to claim 51, wherein said angiotensin II receptor antagonists and angiotensin converting enzyme inhibitors are selected from the group consisting of CS-866, losartan and candesartan, and said insulin resistance improving agents are selected from the group consisting of troglitazone and pioglitazone.

70. The method according to claim 51, wherein insulin resistance improving agents selected from the group consisting of troglitazone and pioglitazone are administered in combination with the angiotensin II receptor antagonist CS-866.

71. The method according to claim 51, wherein said (b) comprises at least one angiotensin II receptor antagonist selected from the group consisting of CS-866, losartan and candesartan; and the insulin resistance improving agent is troglitazone.

72. The method according to claim 51, wherein said (b) is the angiotensin II receptor antagonist CS-866, and the insulin resistance improving agent is troglitazone.

73. The method according to claim 72, wherein the CS-866 is administered in a dose of 2 to 80 mg per day and the troglitazone is administered in a dose of 1 to 1000 mg per day.

74. The method according to claim 51, wherein said (b) is the angiotensin converting enzyme inhibitor temocapril, and the insulin resistance improving agent is troglitazone.

75. The method according to claim 51, wherein said combination of one or more drugs selected from the group consisting of an insulin resistance improving agent and one or more drugs selected from the group consisting of angiotensin II receptor antagonists and angiotensin converting enzyme inhibitors is administered in the form of a combination drug to a mammal suffering from arteriosclerosis.

76. The method according to claim 51, wherein said one or more drugs selected from the group consisting of an insulin resistance improving agent and one or more drugs selected from the group consisting of angiotensin II receptor antagonists and angiotensin converting enzyme inhibitors are administered separately but simultaneously to a mammal suffering from arteriosclerosis.

77. The method according to claim 51, wherein said (a) at least one group consisting of an insulin resistance improving agent or a pharmacologically acceptable salt thereof and (b) at least one drug selected from the group consisting of (i) an angiotensin II receptor antagonist or a pharmacologically acceptable salt thereof and (ii) an angiotensin converting enzyme inhibitor or a pharmacologically acceptable salt thereof are administered separately and non-simultaneously to a mammal suffering from arteriosclerosis.

78. The method according to claim 51, wherein said mammal is a human.

79. The method according to claim 51, wherein the amount of said (a) to the amount of said (b) is in a weight ratio of 1:200 to 200:1.

80. The method according to claim 51, wherein said insulin resistance improving agent is englitazone.

81. The method according to claim 51, wherein said insulin resistance improving agent is BRL-49653.

82. A method for the treatment of arteriosclerosis comprising administering a pharmaceutically effective amount of at least one angiotensin II receptor antagonist selected from the group consisting of CS-866, losartan, candestran, valsartan and irbesartan, or a pharmacologically acceptable salt thereof to a mammal suffering from arteriosclerosis.

83. The method according to claim 82, wherein said angiotensin II receptor antagonist is selected from the group consisting of CS-866, losartan and candestran.

84. The method according to claim 82, wherein said angiotensin II receptor antagonist is CS-866.

85. The method according to claim 82, wherein said angiotensin II receptor antagonist is candestran.

86. The method according to claim 82, wherein the mammal is a human.

\* \* \* \* \*

UNITED STATES PATENT AND TRADEMARK OFFICE
CERTIFICATE OF CORRECTION

PATENT NO. : 6,610,682 B2
DATED : August 26, 2003
INVENTOR(S) : Tsujita et al.

It is certified that error appears in the above-identified patent and that said Letters Patent is hereby corrected as shown below:

Title page,
Item [56], References Cited, OTHER PUBLICATIONS, insert the following:

-- ROTHENTHAL, J., "Therapeutic Experience with Cilazapril", Journal of Cardiovascular Pharmacology, Vol. 24 (Suppl. 2); S65-S69, (1994)

SOMOGYI et al., "A diabetes mellitus es szabad gyokos reakciok feltetelezett kapicsolate az erelmeszesedessel", Orvosi Hetilap, Vol. 135(33); 1815-1818, 8/1994

LEONETTI et al., "Choosing the Right ACE Inhibitor - A Guide to Selection", Drugs, Vol. 49(4); 516-535, 4/1995

WITZUM, J., "Drugs Used in the Treatment of Hyperlipoproteinemias", Chapter 36 of Goodman & Gilman's The Pharmacological Basis of Therapeutics, publ. by McGraw-Hill, pages 875-897, 1996

BELL, D.S., "Insulin Resistance - an often unrecognized problem accompanying chronic medical disorders", Postgraduate Medicine, vol. 93(7); 99-103, 106, 107, 5/1993

MIKI et al., "ACE Inhibitors use in patients with acute coronary syndrome", Japanese Journal of Clinical Medicine, vol. 56(10); 2601-2606, 10/1998 --.

BUHLER et al., "A Vascular Protective Concept in Hypertension and Heart Failure", Journal of Cardiovascular Pharmacology, vol. 24 (suppl. 3); S1-S4, 1994

BONNER, G., "Hyperinsulinemia, Insulin Resistance, and Hypertension", Journal of Cardiovascular Pharmacology, vol. 24 (suppl. 2); S39-S49, 1994

UNITED STATES PATENT AND TRADEMARK OFFICE
CERTIFICATE OF CORRECTION

PATENT NO. : 6,610,682 B2
DATED : August 26, 2003
INVENTOR(S) : Tsujita et al.

It is certified that error appears in the above-identified patent and that said Letters Patent is hereby corrected as shown below:

Title page (cont'd),

"Generalized Cardiovascular Disorders - Chapter 24" from The Merck Manual of Diagnosis and Therapy, Vol. 1 (General Medicine), editor-in-chief Robert Berkow, pages 348-367, 1992

"Anomalies in Lipid Metabolism - Chapter 40" from The Merck Manual of Diagnosis and Therapy, Vol. II (Specialties), editor-in-chief Robert Berkow, pages 624-628, 1992

Schuh, J.R., et al., "Differential Effects of Renin-Angiotensin System Blockade on Atherogenesis in Cholesterol-fed Rabbits, J. Clin. Invest., 91, 1445-1458 (1993)

Signed and Sealed this

Twenty-eighth Day of June, 2005

JON W. DUDAS
*Director of the United States Patent and Trademark Office*